(12) United States Patent
Bauer et al.

(10) Patent No.: US 6,355,844 B1
(45) Date of Patent: *Mar. 12, 2002

(54) PROCESS FOR THE PREPARATION OF MALONDIALDEHYDE-DERIVATIVES

(75) Inventors: Frank Bauer, Bonn (DE); Chitoor Subramaniam, East Brunswick, NJ (US)

(73) Assignee: Creanova, Inc., Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,255

(22) Filed: Jan. 28, 2000

(51) Int. Cl.[7] .................. C07C 43/30; C07C 43/32; C07D 317/22
(52) U.S. Cl. .................. 568/603; 554/227; 549/453
(58) Field of Search .................. 554/227; 549/453; 568/603

(56) References Cited

U.S. PATENT DOCUMENTS

| 2,459,076 A | 1/1949 | Hultquist | 260/615 |
|---|---|---|---|
| 2,823,226 A | 2/1958 | Tsukamoto et al. | 260/488 |
| 3,373,189 A | * 3/1968 | Lum | 260/497 |
| 4,410,733 A | * 10/1983 | Mangold et al. | 568/603 |
| 4,518,785 A | * 5/1985 | Eckhardt et al. | 549/453 |
| 4,647,708 A | * 3/1987 | Hunter et al. | 568/883 |
| 4,655,841 A | 4/1987 | Gerhardt | 106/287.23 |

FOREIGN PATENT DOCUMENTS

EP     0058928     9/1982     C07C/41/54

OTHER PUBLICATIONS

Ullmann's Encyclopedia of Industrial Chemistry, 5th Edition, VCH Verlagsgesellschaft, Weinbeim, vol. A1, p. 36–38.

* cited by examiner

Primary Examiner—Johann Richter
Assistant Examiner—Sikarl A. Witherspoon
(74) Attorney, Agent, or Firm—Abelman, Frayne & Schwab

(57) ABSTRACT

Process for the preparation of malondialdehyde-derivatives by reacting vinylesters with orthoesters in the presence of a precious metal catalyst.

47 Claims, No Drawings

PROCESS FOR THE PREPARATION OF MALONDIALDEHYDE-DERIVATIVES

FIELD OF THE INVENTION

The present invention relates to a process for preparing malondialdehyde-derivatives.

BACKGROUND OF THE INVENTION

Malondialdehyde-derivatives of formula (I):

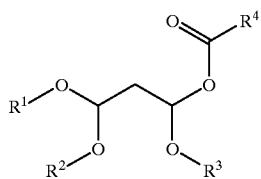

in which $R^1$, $R^2$, $R^3$ and $R^4$ are the same or different alkyl groups, cycbalkyl group, aralkyl groups, or aryl groups, with up to 12 carbon atoms, can be used as intermediates for the preparation of heterocycles, such as pyrazoles, isoxazoles, pyrimidines, 2-aminopyrimidines or pyrimidones. Additionally, at least in those instances where $R^4=CH_3$, the compounds of formula I can be converted to malondialdehyde tetraalkylacetals (U.S. Pat. No. 2,823,226), which aside from their use as organic intermediates, also serve as hardener components for polyvinylalcohol and polyvinylacetate-films (U.S. Pat. No. 4,655,841).

While malondialdehyde tetraalkylacetals can be obtained by directly reacting orthoesters with alkylvinylethers in the presence of suitable Lewis-acids (EP 0058928), the use of alkylvinylethers, on a commercial scale, has several major drawbacks. Methylvinylether, which is needed as the starting material for the preparation of the economically important 1,1,3,3-tetramethoxypropane, is a highly flammable gas that tends to polymerize and, above all, is relatively high priced. Although the higher alkylvinylethers are liquids at room temperature, they are still very expensive and are available to a lesser extent in comparison to vinylesters.

In the preparation of malondialdehyde tetraalkylacetals by Lewis-acid-catalyzed reaction of vinylesters with orthoformates (U.S. Pat. No. 2,459,076), at least 2 moles of orthoester per mole of vinylester must be used in order to achieve acceptable yields. The reaction cannot be halted on the step of the primary addition product of general formula I, since the acid-catalyzed follow-up reaction ($R^5$ stands for $R^1$, $R^2$ and $R^3$) with the orthoester, which is present in the mixture, proceeds faster than the primary addition reaction.

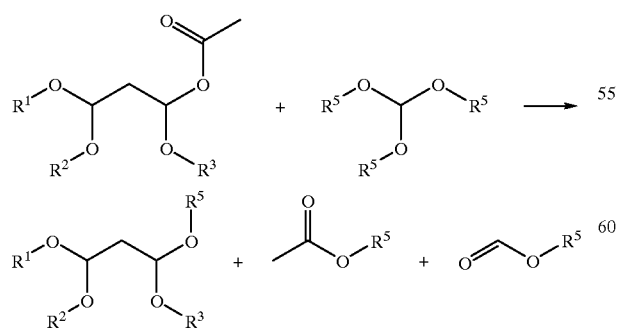

U.S. Pat. No. 2,823,226 deals with this problem. The inventors of the '226 Patent disclose a process which, starting from vinylacetate and orthoformates, basically gives the compounds of formula I with $R^4=CH_3$ without the uneconomical need to use a large excess of orthoester. As suitable catalysts, only mercury-containing catalysts or mixtures of catalysts are mentioned, which have to be used in relatively high concentrations. (For example, the 7.1%, by weight, which is referred to in the '226 Patent is the amount of TMOF used as a starting material.) Because of the high disposal costs of mercury containing residues, the possible contamination of the products with mercury and/or mercury compounds, for regulatory reasons and, most importantly, for ecological reasons, production of the compounds of general formula I according to this process does not make sense.

Thus, a need exists for a process that affords derivatives of malondialdehyde from orthoesters and vinylesters in high yields without the drawback of using mercury-containing catalysts.

SUMMARY OF THE INVENTION

Accordingly, it is an object of the present invention to provide a process for preparing malondialdehyde-derivatives of general formula I:

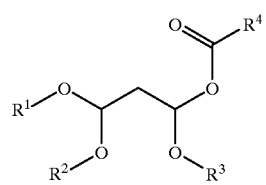

in which $R^1$, $R^2$, $R^3$ and $R^4$ are the same or different alkyl groups, cycloalkyl groups, aralkyl groups or aryl groups, with up to 12 carbon atoms, by reacting vinylesters of general formula II:

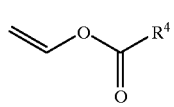

with orthoesters of general formula III:

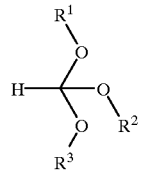

in the presence of a precious metal-catalyst selected from the group consisting of Ru, Rh, Pd, Os, Ir and Pt.

DETAILED DESCRIPTION OF THE INVENTION

The present invention provides a process for preparing malondialdehyde-derivatives of general formula I:

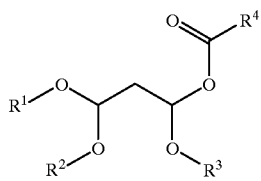

in which $R^1$, $R^2$, $R^3$ and $R^4$ are the same or different alkyl groups, cycloalkyl groups, aralkyl groups, or aryl groups, with up to 12 carbon atoms, from vinylesters and orthoesters without the necessity of using mercury-containing catalysts, It has been found that the foregoing is achieved in a simple manner and that malondialdehyde-derivatives of general formula I are obtained advantageously if a vinylester of general formula II:

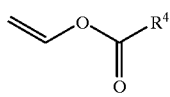

in which $R^4$, as defined above, is reacted with an orthoester of general formula III:

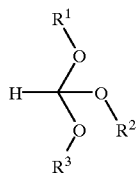

in the presence of a precious metal-catalyst selected from the group consisting of Ru, Rh, Pd Os, Ir and Pt. The use of Pd- and Pt-containing catalysts turned out to be especially advantageous, and as such are preferred, due to their comparably high selectivities and reactivities.

In a preferred embodiment of the process according to the present invention, $R^1$, $R^2$ and $R^3$ identical, especially preferred is the compound of formula I in which $R^1$, $R^2$, $R^3$ and $R^4$ represent a methyl group. In this case, trimethyl orthoformate and vinyl acetate can be used as relatively inexpensive and easily available starting materials. Also, due to the relatively low molecular weight of the protective groups, the resulting 1,1,3-trimethoxy-3-acetoxy-propane is especially suited for the preparation of heterocycles.

It has also been found that the formation of the compounds of general formula I is greatly enhanced by the simultaneous presence of acids, especially of Lewis-acids. The addition of suitable Lewis-acids not only leads to an increase in the reaction rate, but also leads to improved selectivities for the compounds of general formula I. Heterogeneous catalyst-components like acidic aluminas, montmorillonites, ion exchange resins or zeolites, as well as at least partially dissolved halides, such a $ZnCl_2$, $SnCl_4$, $AlCl_3$, $FeCl_3$, $TiCl_4$, $SbF_5$ or compounds that result from these halides by substitution, for example $PhSnCl_3$, can be used an Lewis acids according to a preferred embodiment of the invention. The use of $BF_3$ or $BF_3$-adducts like $BF_3*OEt_2$ or $BF_3*MeOH$ have been found to be especially preferred.

The above described acid-catalyzed follow-up reaction of the compounds of general formula I with the orthoester of general formula III can generally not be totally suppressed under the preferred conditions of the invention, i.e. the presence of one or several Lewis-acids. Also, the presence of the acid leads to at least a partial equilibration of the compounds of general formula I, with the referring malondialdehyde tetraalkyl-acetals of general formula IV and the 1,3-di(alkylcarboxy)-1,3-dialkoxypropanes of general formula V.

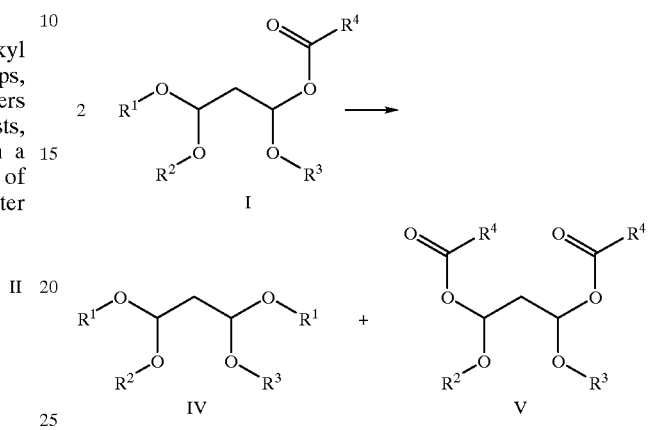

If necessary, the compounds of the general formulas IV and V can be separated from the compounds of general formula I by distillation, thereby giving the latter in pure form. Since upon recycling the compounds of general formula IV and V back into the reaction mixture and with sufficient residence times, they again form the equilibrium mixture of the compounds of general formulas I, IV and V, these byproducts can in principle be completely converted to the product of general formula I. However, since the reaction of the compound of general formula I with the orthoesters of general formula III in not desired, under practical conditions, a slight excess of the malondialdehyde tetraalky-lacetal of general formula IV is normally formed.

In order to suppress the acid-catalyzed side-reactions as much as possible, and since the orthoester is the more expensive starting material, the process according to the invention is preferably conducted with a molar access of the vinylester of general formula II. While in principle there is no limit to the molar excess that can be used, the simultaneously resulting reduction of the space-time-yield leads to a preferred molar excess between about 5% and about 30%.

As can be seen from the above, the reactivity of the precious metal-catalysts, as well as the ratio of the precious metal catalyst-concentration to the Lewis acid(s)-concentration, is of special significance. In order to achieve high yields of the compounds of general formula I, the catalyst-system consisting of the precious metal-catalyst and the Lewis acid must accelerate the primary coupling reaction as much as possible, while, at the same time, the acid-catalyzed follow-up reactions have to be suppressed, as much as possible, by a suitable choice of the acid and minimization of the acid-concentration.

Although it has been found that the malondialdehyde-derivatives of general formula I are detectable when metallic catalysts such as Pt/C and Lewis acids, such as $BF_3$ are present simultaneously, the selectivities and reactivities achieved are unsatisfactory, Compounds of the previously identified precious metals have turned out to be more suitable, especially if they contain the precious metal in an oxidation state >0. The mixture of the compounds of general formulas I, IV and V can be isolated in good yield of, for example, 75% of theoretical with reference to the amount of orthoester used, if precious metal halides, preferably chlorides, and especially preferred chlorides of palladium and/or platinum, or complexes that result from the precious metal chlorides of Pt and Pd are used as the catalyst or as part of the catalyst-system. Examples for such catalysts are $PdCl_2$, $PtCl_2(ACN)_2$, $(NH_4)_2PdCl_4$, $PtCl_2$, $PdCl_4$, $PtCl_4$, $RhCl_3$, $PdCl_2(ACN)_2$, $[RhCl(CO)_2]_2$, $Pd(dba)_2$, $Pd(ACN)_4(BF_4)_2$, $Pt(COD)Cl_2$, $Pd(COD)Cl_2$, $K[PtCl_3(\eta\text{-}C_2H_4)]$, $PdCl_2(PhCN)_2$, $[\pi\text{-}C_3H_5)PdCl]_2$, $PtCl_2(PhCN)_2$, $(NH_4)_2PdCl_6$, $(NH_4)_2PdBr_4$, $[RhCl(C_2H_4)_2]_2$, $(NH_4)_2PdI_4$, $Pd(acac)_2$, $PtCl_2(PPh_3)_2$, $Pt(acac)_2$, etc. Generally, the referenced complexes were found to be superior to the referenced precious metal halides as far as their reactivities and selectivities are concerned. On the one hand, this is due to a better solubility, on the other hand, it is due to an exchange of the ligands with other components of the reaction mixture. It is not surprising that, preferably, neutral ligands that easily exchange with olefins, such as nitriles, ethers, thioethers, olefins, etc., lead to especially high yields of the compounds of general formula I and are therefore preferred.

It has also been found that by the addition of the above ligands as a solvent, improved reactivities can be achieved. The solvent is added to the reaction mixture in amounts of about 0.001 to about 200 percent by weight, preferably in amounts of about 0.1 to about 30 percent by weight. Very high concentrations of the above solvents can, as it has been proven in the case of using acetonitrile in combination with $PdCl_2(ACN)_2$ and $BF_3$-etherate, lead to a reduction in the rate of reaction for the primary coupling reaction.

Also, it is preferable to add polar solvents, such as methylene chloride, which improve the solubility of the precious metal-catalysts, and by means of which positive effects on the reactivity and selectivity of the coupling reaction are achieved.

Obviously, under the conditions of the process according to the present invention, a coordination of the compounds of general formula II to the precious metal or the metal center occurs. Whether the catalytic cycle involves a coordination of the compounds of general formula II, as well as of the compounds of general formula III, is unclear. It was found, however, in the case of $PdCl_2(PhCN)_2$ that by reacting the complex with trimethyl ortho formate, a probably salt-like secondary product was formed that showed poor solubility or no solubility. Whether toluene or vinyl acetate was used as the reaction medium made no difference. The process, according to the invention, therefore explicitly also includes within its scope precious metal compounds that are formed by the reaction of the above precious metals, precious metal halides, or precious metal complexes with the compounds of the general formula I, II, III and/or other components of the reaction mixture.

In order to achieve reaction-times that are acceptable under commercial conditions and in order to suppress the formation of the compounds of general formula IV, the precious metal catalysts normally have to be used in the concentration range of about 0.00001 mol percent to about 200 mole percent, preferably about 0.01 to about 1 mole percent, with reference to the orthoester-component of general formula III. This means that the catalyst-costs greatly influence the economics of the process.

Upon conducting the reaction in homogeneous solution or in suspension, the possibility of increasing the conversion rate by increasing the reaction temperature is limited. For the preferred embodiment of the process according to the invention, it has been found that the primary coupling reaction is normally enhanced to a greater extent by an increase in temperature than the solely acid-catalyzed follow-up reactions. An upper limit for the process, according to the invention, also results from the fragmentation of the orthoesters of general formula III, which is catalyzed by acids (compare to EP 0058928). Even in the presence of relatively mild catalysts, this fragmentation leads to significant yield-losses above 200° C. Below −25° C. the reaction was found, even in the presence of comparably reactive catalysts-systems such as $PtCl_2(ACN)_2/BF_3$, to be too slow for the resulting reaction-times to be acceptable under commercial conditions.

While a continuous reaction of the compounds of general formulas II and III can also be conducted at very high temperatures due to short contact-times, it has been found to be advantageous to conduct the reaction between about 10° C. and to limit the reaction temperature to about 80° C. if the reaction is run purely batch-wise. In this case, the best yields of the compounds of general formula I at reaction times ranging from a few minutes to some hours were normally achieved in the especially preferred temperature range of about 25° C. to about 35° C.

While the compounds of general formulas II and III when added batch-wise and conducted on a laboratory scale can be mixed in any ratio, on a commercial scale it is preferable to feed one starting material to the mixture of the other starting material and the catalyst. This is not only favored by various safety aspects, but also by the fact that the vinylesters of general formula II are sensitive toward polymerization and that the coupling reaction of the compounds of general formulas II and III is exothermic.

The continuous reaction of the compounds of general formulas II and III is preferably conducted on a heterogeneous catalyst in order to minimize the costs related to the supply of the catalyst and to the separation of the products from the catalyst. In addition to the precious metal and/or precious metal compound, the heterogeneous catalyst can comprise an acid-component, preferably a Lewis acid-component. Acid-components which can be suitably employed include acidic catalyst-supports or ion exchange resins, such as acidic alumina, DELOXAN® ASP or acidic montmorillonites, as well as acids that are supported on or bonded to the support. Alternatively, the acid can be within the reaction mixture, in a (partially) dissolved form.

Surprisingly, the process according to the present invention can also be realized in the gas phase, preferably on a heterogeneous catalyst. A special advantage of this proceeding can be seen in the fact that a separation of the product of general formula I, and eventually the formed products of general formulas IV and V from the unreacted starting materials of general formulas II and III, can be achieved by fractional condensation due to markedly different boiling points. Unconverted orthoester and vinylester can, after the complete removal or partial removal of byproducts, be submitted once again to the conditions of reaction.

By use of a heterogeneous catalyst for the gas phase reaction, "leaching", i.e. the slow loss of precious metal (see for example Tang, H. G., Sherrington, D. C., *J. Catal.* (1993), 142 (2), 540–51), which is often observed in the liquid phase, can be avoided to a great extent. The temperature range for the gas phase reaction according to the present invention ranges between about 40° C. and about 250° C., preferably about 60° C. to about 100° C., and most preferably between about 70° C. to about 90° C. In the most preferred temperature range, yield losses due to fragmentation reactions practically do not occur, whereas the desired coupling reaction is already fast enough to allow for the formation of the compounds of general formula I despite short residence times within the reaction zone. In order to avoid a condensation of starting materials and/or products upon reacting the compounds of general formulas II and III in the most preferred temperature range, the reaction mixture must be diluted with sufficient amounts of an inert gas and/or the system has to be run under vacuum. While the resulting dilution of the compounds of general formulas II and III disfavors their coupling reaction, it leads, on the other hand, to a suppression of polymerization reactions which are frequently observed in the condensed phase and which result in a deactivation of the catalyst. In fact, this has to be regarded as a special advantage of the gas phase variant of the process according to the invention.

Whether the process according to the invention is conducted in the gas phase or the liquid phase, it has been found that the reactivities and selectivities, which can be achieved with a given amount of precious metal catalyst, can be improved by the presence of an oxidant. Suitable oxidants can be inorganic, such as $O_2$, OXONE®, $CuCl_2$ or $FeCl_3$, as well as organic, such as dibutyl peroxide. Especially advantageous are oxidants which are capable of oxidizing the precious metals of the group Ru, Rh, Pd, Os, Ir, or Pt to an oxidation state >0. In the case of the liquid phase variant of the process according to the invention, 1,4-benzoquinone has been found to be especially advantageous, whereas in the gas phase variant, the use of gaseous oxidants, preferably oxygen or oxygen-containing gas mixtures, is practical. The use of oxygen in combination with redox-systems like $Cu^+/Cu^{2+}$ which are regenerated by oxygen, led to relatively long catalyst lives, and are, therefore, especially preferred.

The amount of oxidant(s) to be added in order to give advantageous results can vary in wide ranges, from about 0.0001 mole percent to about 10000 mole percent, with reference to the amount of precious metal catalyst. In practice, though, one would normally choose quantities of oxidants which are not unnecessarily high, especially if the oxidant(s) is high boiling, and the reaction is conducted in the liquid phase.

It has been found that the precious metal catalysts showed an improved lifetime, and that smaller amounts of precious metal catalysts could be used without loosing selectivity if low boiling byproducts are being removed during the reaction. On using unreduced catalyst-concentrations, significantly improved selectivities were observed. It turned out to be especially important to remove any formed alkanols like methanol, ethanol, etc. Lower alkanols, above all methanol, can reduce the preferred catalysts according to the invention, such as $PtCl_4$ or $PtCl_2(ACN)_2$, to their metallic state. In a preferred embodiment of the present process, low boiling by-products are, therefore, continuously removed during the reaction. For example, the low boiling impurities can be distilled off by fractional distillation, preferably in vacuo.

When conducting the process according to the present invention using a heterogeneous catalyst, the separation of the products of general formulas I, IV and V from the catalyst can be achieved principally by known methods of mechanical separation, if a fixed-bed is not used. In view of the high value of the claimed precious metal-catalysts, if they are used in at least partially dissolved form, they have to be recovered as quantitatively as possible in a form that allows for their re-use and/or their conversion to the pure precious metal and/or precious metal compounds.

It has been found that in practice there are several available possibilities for achieving this goal. After the completion of the reaction and either before or after a neutralization step with suitable bases like $Na_2CO_3$ has been conducted, the mixture can, for example, be treated with a reducing agent which is capable of converting at least the majority of the precious metal catalyst into the metallic form.

A reduction of the preferred precious metal compounds to the metal and its subsequent mechanical removal from the reaction mixture can be conducted before or after the neutralization which, as described hereafter, is not absolutely necessary at all. When neutralization occurs before the reduction, either some precious metal is being lost with the salt-waste, or a mixture of salt-waste and precious metal is recovered. While a separation of the salt-waste and the precious metal can easily be achieved with water, this leads to the undesired creation of wastewater. Consequently, it is advantageous to carry out the reduction before the neutralization.

The precious metal, which may contain small amounts of salts, if the mixture had been neutralized, can then be separated from the rest of the reaction mixture by a separation technique, such as decanting or filtration. In this way, it is freed more or less of byproducts, but may still be further purified by an appropriate washing-process, preferably using water to remove any residual salts and/or Lewis-acids. Suitable reducing agents must not react with the starting materials, products or byproducts to a significant extent, otherwise their consumption would be unnecessarily high, besides leading to a reduced yield. In practice, the use of $NaBH_4$ as such or dissolved in an appropriate solvent has proven to be effective.

A separation of the precious metal catalysts in the form of the metal suffers from the disadvantage that the exact use of the precious metals in a higher oxidation state was found to be a preferred embodiment of the process according to the invention. As a consequence, a separate conversion of the metals into the preferred precious metal-catalysts becomes necessary eventually.

It has been found, however, that a separation of at least partially dissolved precious metal-catalysts from the products of general formulas I, IV and V, or the remaining starting materials of general formulas II and III, can easily be achieved by distillation. As long as the distillation is conducted under sufficiently mild conditions, i.e. preferably under vacuum and especially preferred under vacuum using a short path evaporator, thin film evaporator, or a wiped film evaporator, a neutralization of dissolved Lewis-acids is not required. In order to minimize any deactivation of the preferred precious metal catalysts and/or Lewis acids, such neutralization is not employed.

The obtained distillation residue can, after an eventual making-up of Lewis acid, be re-used as a catalyst for the process according to the invention. However, in practice, it has been found that the residue normally exhibits a reduced reactivity compared to the original catalyst, with respect to the original catalyst-system. This deactivation can be suppressed by the addition of the above oxidants, either before, during and/or after the distillation. It has been found to be especially advantageous, in addition, to add sufficiently soluble halides like LiCl and/or ligands like acetonitrile, which attached to the precious metal center, easily exchange with olefins and, thereby, generate or regenerate the especially preferred precious metal-catalysts according to the process of the invention.

The amount of precious metal catalyst, which upon this preferred embodiment of the process according to the invention, has to be removed and worked-up externally, depends ultimately on the amount of high-boilers which, on distillative isolation of the malondialdehyde-derivatives, remain as residue together with the precious metal catalyst and the catalyst-system, respectively. In order to minimize the amount of residue and, thereby, significantly improve the economics of the process according to the invention, without losing any compounds of general formulas I, II, III, IV and V, its further reduction can be achieved in a second distillation step. This allows for the choice of an increased pot temperature and/or an improved vacuum on the second distillation step, which allows again for the advantageous use of a short path evaporator, a thin film evaporator, or a wiped film evaporator. Furthermore, the preferred precious metal-catalysts and, especially any added organic oxidants like 1,4-benzoquinone, tend to breakdown at high temperatures.

Having described the present invention, reference will now be made to the following examples which are provided solely for purposes of illustration and are not intended to be limiting.

EXAMPLE 1

1,1,3-Trimethoxy-3-acetoxypropane

To 50.0 g (0.58 mole) of vinylacetate stirred at 20° C., 100 mg 1,4-benzo-quinone and 100 mg $PtCl_2(PhCN)_2$ were added successively. After 5 minutes, 53.0 g (0.50 mole) of trimethyl ortho formate and 200 mg $BF_3*OEt_2$ were fed. The initially muddy mixture, which later became clear, was maintained at 30° C. for 24 hours. A gas chromatographic analysis of the mixture, after neutralization with excess anhydrous sodium carbonate, revealed a full conversion of the trimethyl ortho formate. The ratio of 1,1,3,3-tetramethoxypropane to 1-acetoxy-1,3,3-trimethoxypropane, and the isomeric 1,3-diacetoxy-1,3-dimethoxy-propanes was determined to be 8.2:11.2:1.0 on the basis of the FID-area-percentages. The mixture still contained excess vinylacetate.

EXAMPLE 2

1,1,3-Trimethoxy-3-acetoxypropane

The same procedure was followed as in example 1, except that 1.00 g $PdCl_2(ACN)_2$ and 0.65 g $BF_3*OEt_2$ were used as the catalyst-system. The reaction mixture turned black within a few minutes due to precipitation of metallic palladium. After 2.0 hours, excess sodium carbonate was added. The resulting suspension was stirred for 20 minutes further and then filtered using a folding-filter. By fractional vacuum-distillation (8 mbar) 70.0 g of a clear colorless mixture, comprising of 1,1,3,3-tetramethoxypropane, 1-acetoxy-1,3,3-trimethoxypropane and the isomeric 1,3-diacetoxy-1,3-dimethoxypropanes, could be isolated. The ratio of 1,1,3,3-tetramethoxypropane to 1-acetoxy-1,3,3-trimethoxypropane and the isomeric 1,3-diacetoxy-1,3-dimethoxypropanes was determined to be 6:3:1 by gas chromatography. This refers to the total yield of malondialdehyde-derivatives of 75% of theoretical with reference to the amount of trimethyl orthoformate.

EXAMPLE 3

1,1,3-Trimethoxy-3-acetoxypropane

To 50.0 g (0.58 mole) of vinylacetate stirred at 20° C., 200 mg 1,4-benzo-quinone and 500 mg $PdCl_2(ACN)_2$ were added successively. After 5 minutes, 53.0 g (0.50 mole) of trimethyl ortho formate and 350 mg $BF_3*OEt_2$ were fed. The mixture remained clear during the entire reaction time. After 2.0 hours, the mixture was worked-up as described in example 2, and the malondialdehyde-derivatives isolated were 76% of theoretical with reference to the amount of trimethyl ortho formate.

EXAMPLE 4

1,1,3-Trimethoxy-3-acetoxypropane

The same procedure was followed as in example 3, except that the batch-size was increased by a factor of 5. By subsequent distillative product-isolation using a short path evaporator, the malondialdehyde-derivatives isolated were 80% of theoretical with reference to the amount of trimethyl ortho formate,

EXAMPLE 5

1,1,3-Trimethoxy-3-acetoxypropane

A mixture of 56.00 g trimethyl ortho formate, 60.00 g vinylacetate, 0.75 g $PdCl_2(ACN)_2$, 0.60 g 1,4-benzoquinone, and 1.00 ml $BF_3*OEt_2$ was stirred at 30° C., and low boiling impurities were removed from the reaction mixture through the application of a slight vacuum. A fractionation column was installed to prevent losses of starting materials and/or products. After 2.3 hours, the ratio of 1,1,3,3-tetramethoxypropane to 1-acetoxy-1,3,3-trimethoxypropane, and the isomeric 1,3-diacetoxy-1,3-dimethoxy-propanes was determined by CG-analysis to be 1.0:2.4:1.3 on the basis of the FID-area-percentages. In a comparative experiment, without removal of low boiling impurities, the referring ratio was determined to be 1.0:1.48:0.50. Both reaction mixtures still contained an excess of vinylacetate.

EXAMPLE 6

1,1,3-Triethoxy-3-acetoxypropane

The same procedure was followed as in example 1, except that the trimethyl ortho formate was substituted by 74.1 g (0.50 mole) triethyl ortho formate. 800 mg $(NH_4)_2PdCl_4$, and 660 mg $BF_3*OEt_2$ were used as the catalyst-system. The majority of the set-in precious metal complex was either not dissolved or formed non-dissolvable follow-up products under the reaction conditions. By GC/MS-analysis of the neutralized reaction mixture after completion of the reaction, the formation of 1,1,3,3-tetraethoxypropane, 1-acetoxy-1,3,3-triethoxypropane, and the isomeric 1,3-diacetoxy-1,3-diethoxypropanes in a ratio of 14:14:1 (data based on FID-area-percentages) was proven. Further products were not detectable, but the mixture still contained significant amounts of triethyl ortho formate besides the vinylacetate-excess.

EXAMPLE 7

1,1,3-Trimethoxy-3-acetoxypropane

To a mixture of 2.0 g (0.02 mole) of vinylacetate and 2.12 g (0.02 mole) of trimethyl ortho formate stirred at 25° C., 1.0 g of a heterogeneous catalyst was added and the resulting mixture was stirred for 2.0 hours. After separation of the catalyst by filtration, the remaining clear solution was analyzed by gas chromatography. Besides non-converted vinylacetate and trimethyl ortho formate the formation of 1,1,3,3-tetramethoxy-propane, 1-acetoxy-1,3,3-trimethoxypropane, and the isomeric 1,3-diacetoxy-1,3-dimethoxypropanes were detected.

The heterogeneous catalyst was prepared by successive treatment of DELOXAN® ASP I/7, with a solution of PdCl$_2$(ACN)$_2$, ZnCl$_2$ and CuCl$_2$ in acetonitrile, a mixture of trimethyl ortho formate and BF$_3$*OEt$_2$ and pure trimethyl ortho formate. In order to remove the orthoester from the catalyst, it was subsequently dried at 65° C./0.5 mm until the weight remained constant.

EXAMPLE 8

1,1,3-Trimethoxy-3-acetoxypropane

A mixture of 50.0 g (0.58 mole) of vinylacetate and 53.0 g (0.50 mole) of trimethyl orthoformate was continuously evaporated into a vacuum-line (30 mbar) within 1.0 hours. The gas mixture was passed over a heated (80° C.) fixed-bed catalyst (length of catalyst-bed: 10 cm; diameter of catalyst-bed: 2 cm). By condensation at −78° C., 101.9 g product-mixture were received. A gas chromatographic analysis showed the formation of 1,3,3-trimethoxy-1-acetoxypropane and 1,1,3,3-tetramethoxy-propane in a ratio of 1:1. By quantification of the non-converted trimethyl orthoformate as well as the products, the trimethyl orthoformate-losses due to fragmentation and other side reactions were calculated to be only 2.0%.

The heterogeneous catalyst was prepared by doping an inert support with 3.0 g PdCl$_2$(ACN)$_2$, 5.0 g ZnCl$_2$, and 1.0 g CuCl$_2$. 1000 g of acetonitrile were used as the solvent. Before its use, the catalyst was conditioned with 1.0 g BF$_3$*OEt$_2$ and 25.0 g trimethyl ortho formate and subsequently dried for 3.0 hours at 80° C./oil pump vacuum in order to remove the excess of reagents.

EXAMPLE 9

1,1,3-Trimethoxy-3-acetoxypropane

To a mixture of 2.00 g (0.02 mole) of vinylacetate and 2.12 g (0.02 mole) trimethyl ortho formate stirred at 25° C., 20 mg 1,4-benzoquinone and 100 mg [RhCl(CO)$_2$]$_2$ were added successively. After 5 minutes, 100 mg BF$_3$*OEt$_2$ were fed. After that, the mixture was stirred at 30° C. for 2.0 hours before it was neutralized by the addition of excess anhydrous sodium carbonate. A gas chromatographic analysis of the supernatant liquid showed the formation of 1-acetoxy-1,3,3-trimethoxypropane, besides 1,1,3,3-tetramethoxypropane and the isomeric 1,3-diacetoxy-1,3-dimethoxypropanes.

EXAMPLE 10

Pyrazole

To a mixture of 18.8 g hydrazin*HCl, 28.2 g de-ionized water and 3.2 g concentrated HCl, stirred at 30° C., the distilled mixture of malondialdehyde-derivatives from example 2 were fed within 20 minutes. The mixture was stirred for another 1.0 hour at 30° C., then 27.0 g aqueous NaOH (50%) were added with cooling, and the mixture was allowed to stand overnight. By vacuum distillation, 12.9 g pyrazole (69% of theoretical with reference to the set-in amount of malondialdehyde-derivatives) having a boiling-range 95° C. to 105° C./30 mbar was received.

What is claimed is:

1. A process for preparing malondialdehyde-derivatives of general formula I:

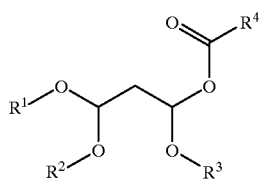

in which R$^1$, R$^2$, R$^3$ and R$^4$ are the same or different alkyl groups, cycloalkyl groups, aralkyl groups, or aryl groups, with up to 12 carbon atoms, which comprises reacting a vinylester of general formula II:

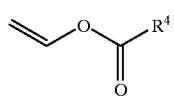

in which R$^4$ is as defined above, with an orthoester of general formula III:

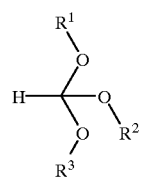

in the presence of a precious metal-catalyst selected from the group consisting of Ru, Rh, Pd, Os, Ir, and Pt.

2. The process of claim 1, wherein the precious metal-catalysts are Pd-based or Pt-based.

3. The process of claim 1, wherein the precious metal exhibits an oxidation state >0.

4. The process of claim 2, wherein the Pd-based or Pt-based catalyst has a +2 oxidation state.

5. The process of claim 1, wherein the reaction is conducted in the presence of an acid.

6. The process of claim 1, wherein the reaction is conducted in the presence of a Lewis acid.

7. The process of claim 2, wherein the reaction is carried out in the presence of a Lewis acid.

8. The process of claim 1, wherein the reaction is conducted in a homogeneous solution or in a suspension.

9. The process of claim 7, wherein BF$_3$ or BF$_3$-adducts are selected from the group consisting of BF$_3$*OEt$_2$ or BF$_3$*MeOH are used as the Lewis acid.

10. The process of claim 1, wherein the precious metal catalyst is a halide in accordance with the formula M(hal)x in which M=a cation of a precious metal selected from the group consisting of Ru, Rh, Pd, Os, Ir and Pt, hal=halide and x is 1 to 6.

11. The process of claim 10, wherein the precious metal halide catalyst is a complex.

12. The process of claim 11, wherein the precious metal halide complexes are selected from the group consisting of chlorides of Pt and Pd.

13. The process of claim 12, wherein the chloride complexes of Pt and Pd are selected from the group consisting of PdCl$_2$, PtCl$_2$(ACN)$_2$, (NH$_4$)$_2$PdCl$_4$, PtCl$_2$, PdCl$_4$, PtCl$_4$, RhCl$_3$, PdCl$_2$(ACN)$_2$, [RhCl(CO)$_2$]$_2$, Pd(dba)$_2$, Pd(ACN)$_4$(BF$_4$)$_2$, Pt(COD)Cl$_2$, Pd(COD)Cl$_2$, K[PtCl$_3$(η-C$_2$H$_4$)], PdCl$_2$(PhCN)$_2$, [π-C$_3$H$_5$)PdCl]$_2$, PtCl$_2$(PhCN)$_2$, (NH$_4$)$_2$PdCl$_6$, (NH$_4$)$_2$PdBr$_4$, [RhCl(C$_2$H$_4$)$_2$]$_2$, (NH$_4$)$_2$PdI$_4$, Pd(acac)$_2$, PtCl$_2$(PPh$_3$)$_2$, and Pt(acac)$_2$.

14. The process of claim 1, wherein the precious metal catalyst is present in a concentration range of about 0.00001 to about 200 mole percent, with reference to the orthoester of general formula III.

15. The process of claim 14, wherein the precious metal catalyst is present in a concentration range of about 0.01 to about 1 mole percent based on the orthoester component of general formula III.

16. The process of claim 1, wherein the reaction is conducted in the presence of a solvent.

17. The process of claim 16, wherein the solvent is polar.

18. The process of claim 16, wherein the solvent is the source of ligands.

19. The process of claim 1, wherein the reaction is conducted in the range of about −25° C. to about 200° C.

20. The process of claim 19, wherein the reaction is conducted in the range of about 10° C. to about 80° C.

21. The process of claim 20, wherein the reaction is conducted in the range of about 25° C. to about 35° C.

22. The process of claim 1, wherein the compound of general formula II is used in excess with reference to the compound of general formula III.

23. The process of claim 22, wherein the compound of general formula II is used from about 5 to about 30 mole percent in excess with reference to the compound of general formula III.

24. The process of claim 1, wherein low boiling by-products are continuously or semi-continuously removed from the reaction mixture by distillation.

25. The process of claim 24, wherein the distillation is fractional distillation.

26. The process of claim 25, wherein the fractional distillation is conducted in vacuo.

27. The process of claim 1, wherein one of the starting materials of general formulas II and III is fed to the mixture of the other starting material and the catalyst.

28. The process of claim 27, wherein the orthoester of formula III is fed to the mixture of formula II.

29. The process of claim 13, wherein a reducing agent capable of converting the majority of the precious metal catalyst into the metallic form is added to the reaction mixture after the reaction is complete, whereby the reaction mixture is liberated from the precious metal by mechanical separation.

30. The process of claim 29, including an inert support whereby the reaction mixture is liberated from the supported precious metal by mechanical separation.

31. The process of claim 30, wherein the reducing agent is NaBH$_4$ and the inert support is active charcoal.

32. The process of claim 29, wherein the reducing agent is hydrogen or CO.

33. The process of claim 1, wherein the catalyst is a heterogeneous catalyst.

34. The process of claim 33, wherein the heterogeneous catalyst is also an acid component.

35. The process of claim 34, wherein the acid component is a Lewis acid.

36. The process of claim 33, wherein the reaction is conducted in the gas phase.

37. The process of claim 35, wherein the reaction temperature is between about 40° C. and about 250° C.; and wherein a vacuum is applied, or an inert gas is added, or a vacuum is applied and a gas is added, in order to prevent condensation of the starting materials, the products, or both.

38. The process of claim 36, wherein separation of the product is achieved by fractional condensation and, wherein, unconverted starting material of general formulas II and/or III are again submitted to the reaction conditions.

39. The process of claim 1, wherein the reaction is conducted in the presence of 0.0001 to 10000 mole percent, based on the amount of precious metal-catalyst, of an organic or inorganic oxidant that is capable of oxidizing the precious metals and re-oxidizing any precious metals that have been formed from the precious metal compounds.

40. The process of claim 39, wherein oxygen or mixtures containing oxygen are used as the oxidant, and wherein the addition of a suitable co-catalyst guarantees the efficient oxidation of the precious metals and/or the efficient re-oxidation of the precious metals that have been formed from precious metal compounds.

41. The process of claim 1, wherein the products of general formula IV:

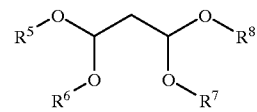

and general formula V:

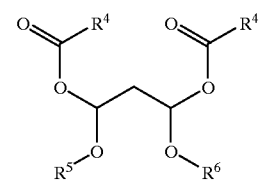

are formed and in which R$^5$, R$^6$, R$^7$ and R$^8$ independently represent one of the groups R$^1$, R$^2$ or R$^3$ and are separated from the products of general formula I by distillation and recycled.

42. The process of claims 41, wherein the mixture of compounds of general formula I and the byproducts of general formulas IV and V are used as starting materials for the synthesis of secondary products without a prior separation.

43. The process of claim 41, wherein the compounds of general formula I, or the mixture of the compounds of general formula I and the compounds of general formulas IV and V are converted to malondialdehyde tetraalkyl-, tetracycloalkyl-, tetraaryl-, and tetraaralkyl-acetals by an acid-catalyzed reaction with alkyl alcohols.

44. A process for preparing malondialdehyde derivatives of general formula I:

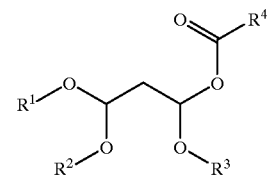

in which R$^1$, R$^2$, R$^3$ and R$^4$ are the same or different alkyl groups, cycloalkyl groups, aralkyl groups, or aryl groups, with up to 12 carbon atoms, which comprises reacting a vinylester of general formula II:

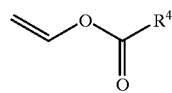

in which R⁴ is as defined above, with an orthoester of general formula III:

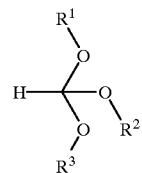

in the presence of a precious metal-catalyst selected from the group consisting of Ru, Rh, Pd, Os, Ir, and Pt; and isolating the compounds of general formula I and the compounds of general formula IV

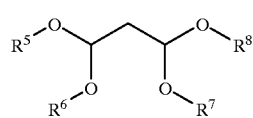

and V

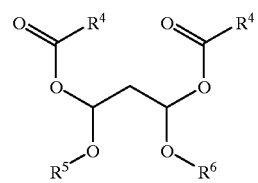

by distillation after neutralization of the reaction mixture with a base.

45. The process of claim 44, wherein the distillative product-isolation is conducted under vacuum by a member selected from the group consisting of a short path evaporator, a thin film evaporator, or a wiped film evaporator, without prior neutralization.

46. The process of claim 45, wherein the distillation residue containing the precious metal catalyst is re-used as a catalyst in the process, whereby an oxidant, a halide, or both are added before, during, or after the distillation, or any combination thereof.

47. The process of claim 45, wherein the amount of distillation residue is reduced in a second distillation step at an increased distillation temperature and/or under improved vacuum using a short path evaporator, a thin film evaporator, or a wiped film evaporator.

* * * * *